(12) United States Patent
Miyata

(10) Patent No.: US 6,636,299 B1
(45) Date of Patent: Oct. 21, 2003

(54) INTRAOCULAR LENS INSPECTION METHOD

(76) Inventor: Akira Miyata, 22-32, Inokuchidai 2-chome, Nishi-ku, Hiroshima-shi, Hiroshima (JP)

( * ) Notice: Subject to any disclaimer, the term of this patent is extended or adjusted under 35 U.S.C. 154(b) by 0 days.

(21) Appl. No.: 10/123,668

(22) Filed: Apr. 16, 2002

(51) Int. Cl.[7] .................................................. G01B 9/00
(52) U.S. Cl. ....................................................... 356/124
(58) Field of Search ............................... 356/124, 124.5, 356/125; 250/461.1, 459.1, 458.1

(56) References Cited

U.S. PATENT DOCUMENTS

| | | | | |
|---|---|---|---|---|
| 4,213,701 A | * | 7/1980 | Lanzilloti | 356/124 |
| 5,633,504 A | * | 5/1997 | Collins et al. | 250/461.1 |
| 6,455,318 B1 | * | 9/2002 | Chan | 436/86 |

* cited by examiner

Primary Examiner—Michael P. Stafira
(74) Attorney, Agent, or Firm—Koda & Androlia

(57) ABSTRACT

An intraocular lens inspection method including: a process of extracting an intraocular lens for inspection for selecting an intraocular lens; this lens is next, in high temperature liquid immersion process, immersed in physiological saline and kept for a specific amount of time at high temperature that would not deteriorate the lens; then in low-temperature liquid immersion process, the lens is removed and transferred to physiological saline kept at low temperature, which is approximately the temperature when clinically used, and the lens is observed macroscopically; and then in inspection process the lens is put in a chamber kept at the same low temperature, its surface is washed and observed by a microscope, and after observation, the lens is returned to its original state, and when the changes are observed over time and consistent glistenings are detected with each observation, it is judged that clinically analogous glistenings will develop.

1 Claim, 5 Drawing Sheets

INTRAOCULAR LENS INSPECTION METHOD

BACKGROUND OF THE INVENTION

1. Field of the Invention

The present invention relates to a method for inspecting an intraocular lens, also called an artificial crystalline lens, which is inserted after lensectomy during cataract surgery and has the function of a convex lens, and particularly to an intraocular lens inspection method that makes it possible to judge whether or not a lens should be accepted for or rejected from use by checking for the presence and the extent of glistenings prior to clinical use.

2. Prior Art

There are conventional methods of inspecting intraocular lenses in terms of their properties, optics, sterility, etc. As discussed in "Glistenings in Acrylic Lenses" in the *Rinsho Ganka*—Japanese Journal of Ophthalmology, Vol. 51, No. 4, 1997, the effect on visual performance of the intraocular lenses made from a lens body of an acrylic copolymer cross-linked resin, also called acrylic lenses, used in small-incision sutureless surgery, particularly the development of glistenings seen in clinical cases having a diameter of 10 to 20 μm, has recently been energetically investigated. However, an intraocular lens inspection method has not been established with which it is possible to evaluate whether or not a lens should be accepted for or rejected from use prior to clinical use.

A method of inspecting intraocular lenses prior to clinical use has not been established by conventional intraocular lens inspection methods. Therefore, there is a problem in that although the risk is known of glistenings developing due to internal structure, such as voids, etc., depending on the materials and production method used, direct use clinically without knowing the extent or status, etc., of the glistenings is unavoidable.

FIG. 5A and FIG. 5B show intraocular lens 1 made from a lens body of acrylic copolymer cross-linked resin, also called an acrylic lens, used in small incision sutureless surgery. The intraocular lens 1 is comprised of a lens body 1a and two loops 1b that hold this lens body at the posterior chamber. Lens diameter of this lens body is 5.5 to 6 mm, and maximum diameter of these two loops is approximately 13 mm. This lens body is made from an acrylic copolymer cross-linked resin having a three-dimensional structure wherein copolymer of phenylethyl acrylate and phenylethyl methacrylate is cross-linked by butanediol diacrylate. It has a reflective index of 1.55 and shows ultraviolet ray-absorbing capability. It is flexible with a Shore hardness (Shore A), which represents surface hardness, of 45. As shown in FIG. 6, it can be folded in two. With respect to thermal properties, its glass transition temperature $T_g$ is 15.5–21.5° C., with there being a marked increase in volume expansion at this transition temperature $T_g$ or higher when compared to volume expansion at temperatures lower than $T_g$.

As shown in the histogram in FIG. 7 of the clinical glistening development period when a conventional acrylic copolymer cross-linked resin intraocular lens was used, development of glistenings during the post-surgical observation period (density of approximately 50 glistenings or more, clinical classification grade one or higher) was confirmed in 28 of 49 eyes (57%). Moreover, when the time at which the development of these glistenings was first confirmed serves as the glistening development period, there were no cases in which glistenings developed one month after surgery, but there were cases in which glistenings developed two months after surgery or later, with the greatest delay in the development of glistenings being 16 months after surgery. The average glistening development period in these 28 eyes was 6.6 months; and when clinical classification is grade 0=0 glistenings/mm$^3$, grade 1=50 glistenings/mm$^3$, grade 2=100 glistenings/mm$^3$, and grade 3=200 glistenings/mm$^3$, then the density of these glistenings covers a broad range of grade 1, grade 2, and grade 3. Today we are in the stage of energetically investigating the effect of these glistenings on visual function with respect to a variety of indicators, including visual acuity, glare, contrast, etc.

There have been no reports of cases of glistenings when conventional polymethyl methacrylate (PMMA) resin intraocular lenses have been clinically used. However, these intraocular lenses are rigid and cannot be folded in half; and therefore, there is a disadvantage in that the surgical incision is wide and they are not suitable for small-incision sutureless surgery. Furthermore, there is a double disadvantage in that the refractive index of PMMA resin is 1.49, which is smaller than the refractive index of 1.55 of the above-described acrylic copolymer cross-linked resin; and in order to obtain a lens of the same power, a thick lens of thickness d is required. Therefore, the frequency with which PMMA resin intraocular lenses are used has recently decreased.

SUMMARY OF THE INVENTION

In order to solve the above-described problems, the intraocular lens inspection method of the present invention is characterized in that an intraocular lens to be inspected is extracted randomly from an intraocular lens production lot prior to clinical use, the intraocular lens that has thus been selected is kept for a specific amount of time in physiological saline at a high-temperature and then promptly transferred to physiological saline that has been kept at a low-temperature, then the lens is examined for glistenings by being magnified and observed over time, and when a consistent number and size of glistenings are seen, it is judged that clinically analogous glistening will develop.

DETAILED DESCRIPTION OF THE INVENTION

Figure 1:
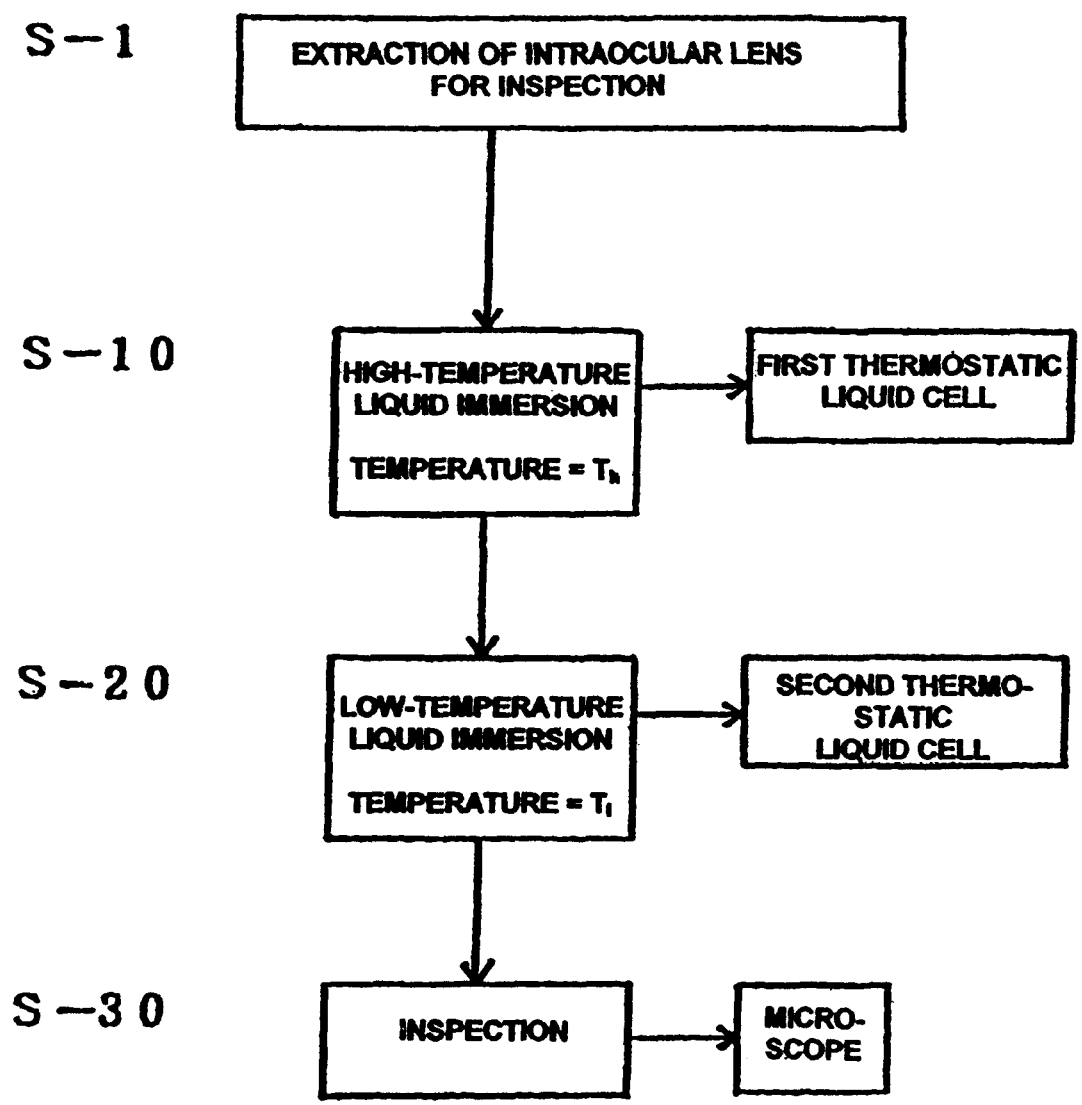
FIG. 1 is a flowchart showing the processes of an embodiment of the intraocular lens inspection method of the present invention.

The intraocular lens inspecting method of the present invention is characterized in that:

an inspection intraocular lens extracting process (S-1) is first executed so as to extract an intraocular lens for inspection whereby a plurality of intraocular lenses are selected by random extraction from an intraocular lens production lot;

next in a high-temperature liquid immersion process (S-10), the intraocular lens that has been extracted is immersed in physiological saline which is a sterile aqueous sodium chloride solution isotonic with the same environmental body fluid as when clinically used and kept for a specific amount of time at high temperature $T_h$ such that deterioration of the lens does not occur using a first thermostatic liquid cell such as an incubator, which is a thermostatic cultivation device, etc.;

then promptly moving to a low-temperature liquid immersion process (S-20) wherein the intraocular lens is removed and transferred to physiological saline that has been kept at low temperature $T_l$ which is approximately the same temperature as when clinically used, using a second thermostatic liquid cell, and the intraocular lens is observed macroscopically; and in an inspection process (S-30), if changes are difficult to see, the intraocular lens is removed to inside a chamber kept at the low-temperature $T_l$, the surface is gently washed and magnified and observed under a microscope and after observation, the intraocular lens is quickly returned to its original state, and when these changes are observed over time and glistenings that are consistent in terms of the number and size are observed with each of these observations, it is judged that clinically analogous glistenings will develop.

In the intraocular lens inspection method of the present invention, it is also possible to use a liquid cell inside a thermostatic chamber kept at low-temperature $T_l$ as the second thermostatic liquid cell used in the low-temperature liquid immersion process (S-20).

The intraocular lens is removed from the chamber kept at low temperature $T_l$, and the lens surface is gently washed with distilled water at the same temperature $T_l$ during the inspection process (S-30). This inspection process (S-30) of the intraocular lens inspection method of the present invention has the effect of avoiding temperature changes and preventing precipitation of salt crystals from the physiological saline onto this lens surface.

In the microscope in inspection process (S-30) of the intraocular lens inspection method of the present invention, a slit-lamp microscope normally used by ophthalmologists can be used for magnification and observation. It is possible to check for changes over time by holding the intraocular lens that is to be inspected on the holder of this slit-lamp microscope, illuminating light from an illumination lamp onto the lens surface oblique from the illumination optical axis using a mirror, and magnifying and observing the lens using a microscope.

When the intraocular lens inspection method of the present invention is used on an intraocular lens made from an acrylic copolymer cross-linked resin also called an acrylic lens, then glistenings analogous to those that develop in clinical cases can be found in several days. On the average, the development period in clinical cases is as long as six months. However, by using this intraocular lens inspection method, it is possible to judge whether or not a lens should be accepted for or rejected from use prior to clinical use, thus avoiding clinical risks and inspecting a lens with the glistening development period being markedly curtailed.

The reason why the glistening development period can be markedly curtailed when the intraocular lens inspection method of the present invention is applied to acrylic copolymer cross-linked resin intraocular lenses is that resins made from a three-dimensional structure such as acrylic copolymer cross-linked resin comprise continuous hollow structures on the inside also called voids; and when the lens is kept for a specific amount of time at high temperature $T_h$ of the glass transition temperature $T_g$ of this resin of 15.5 to 21.5° C. or higher, or approximately 50° C., during the high-temperature liquid immersion process (S-10), there is a marked increase in volume expansion with the solution in the surrounding environment being suctioned into this continuous hollow structure that has inflated; and when kept at low-temperature $T_l$ during the low-temperature liquid immersion process (S-20) that provides the same ambient temperature as when clinically used, then volume contraction takes place and the liquid that has been suctioned is emitted; and even under steady-state conditions, solution components in small granule form are left behind and glistening is displayed due to the difference from the surrounding refractive index. This type of sudden temperature change does not occur in clinical examples; and therefore, the glistening development period is delayed considerably. It can also be assumed that there will be considerable variation from individual to individual over the long run.

When the intraocular lens inspection method of the present invention was used for intraocular lenses the lens body of which is made from polymethyl methacrylate, no development of even some glistening was observed. Also, there are no reported cases of the development of glistenings, even when this intraocular lens is used clinically. Therefore, such lenses were not in contradiction to this intraocular lens inspection method.

Figure 2A:
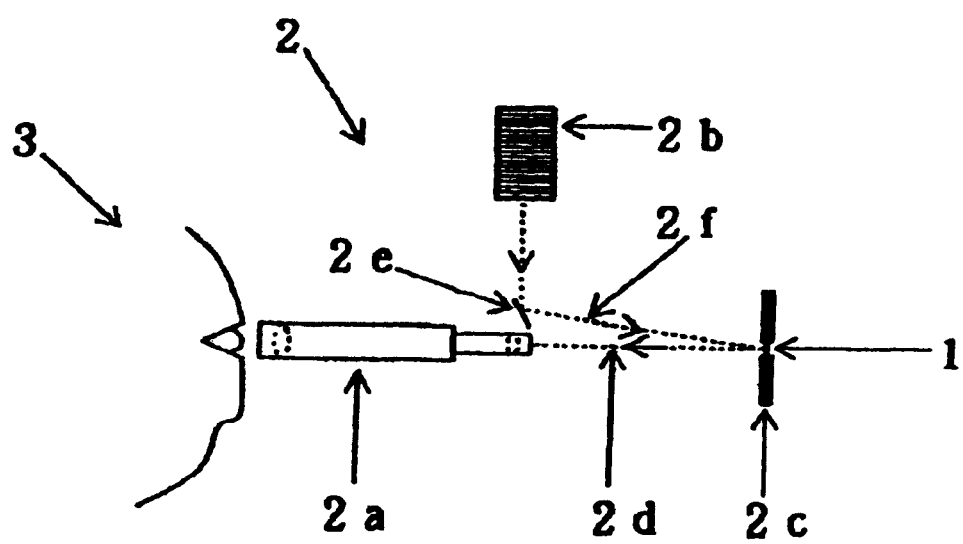
FIG. 2A is a side view of part of the inspection mechanism for observing glistenings of an embodiment of the intraocular lens inspection method of the present invention that uses a slit-lamp microscope.
Figure 2B:
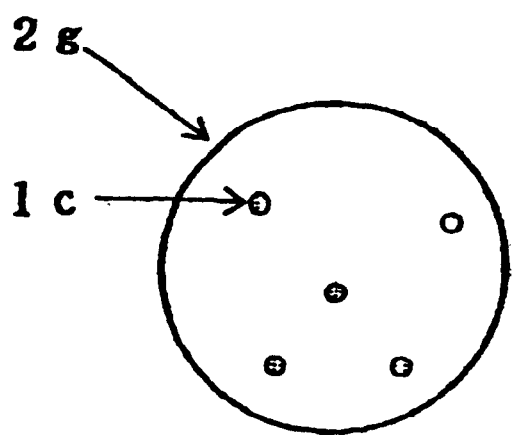
FIG. 2B is an example of the field in which the intraocular land surface for inspection is inspected and observed with a microscope.
Figure 3:
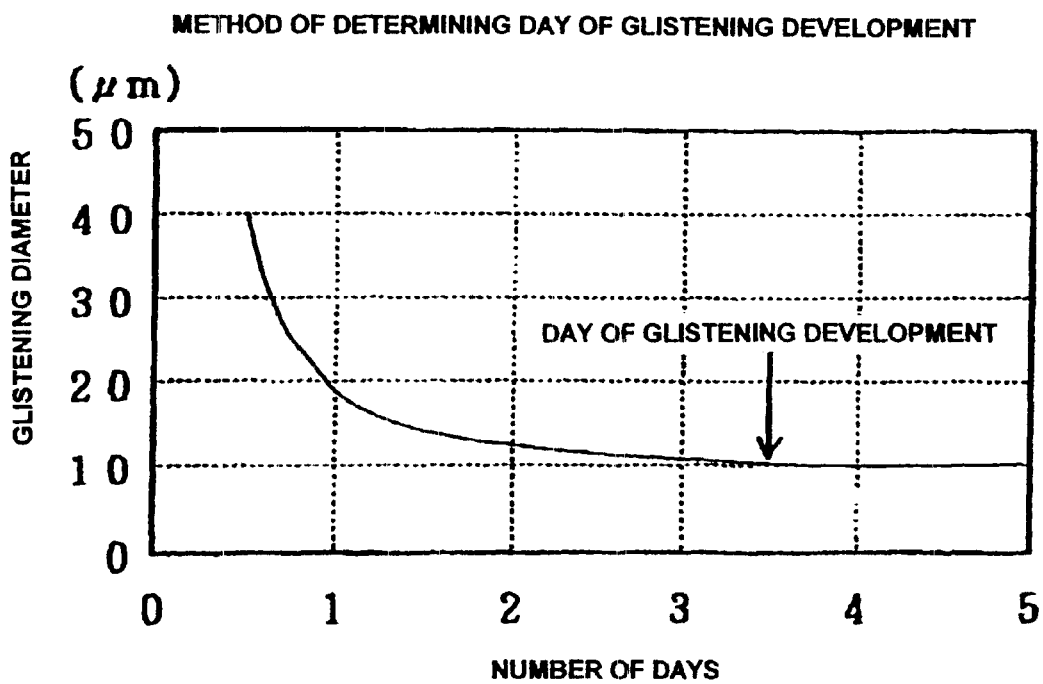
FIG. 3 shows the changes over time in glistening diameter using microscopic observation showing a method of determining the day of glistening development by an embodiment of the intraocular lens inspection method of the present invention.
Figure 4:
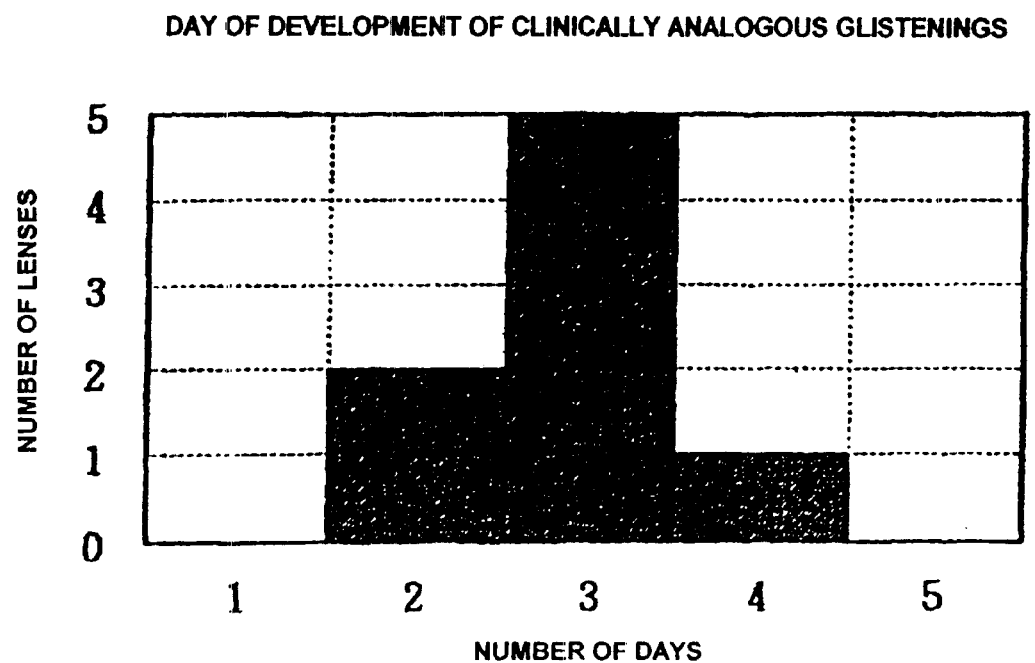
FIG. 4 is a histogram of the day on which clinically analogous glistenings develop as determined using an embodiment of the intraocular lens inspection method of the present invention.
Figure 5A:
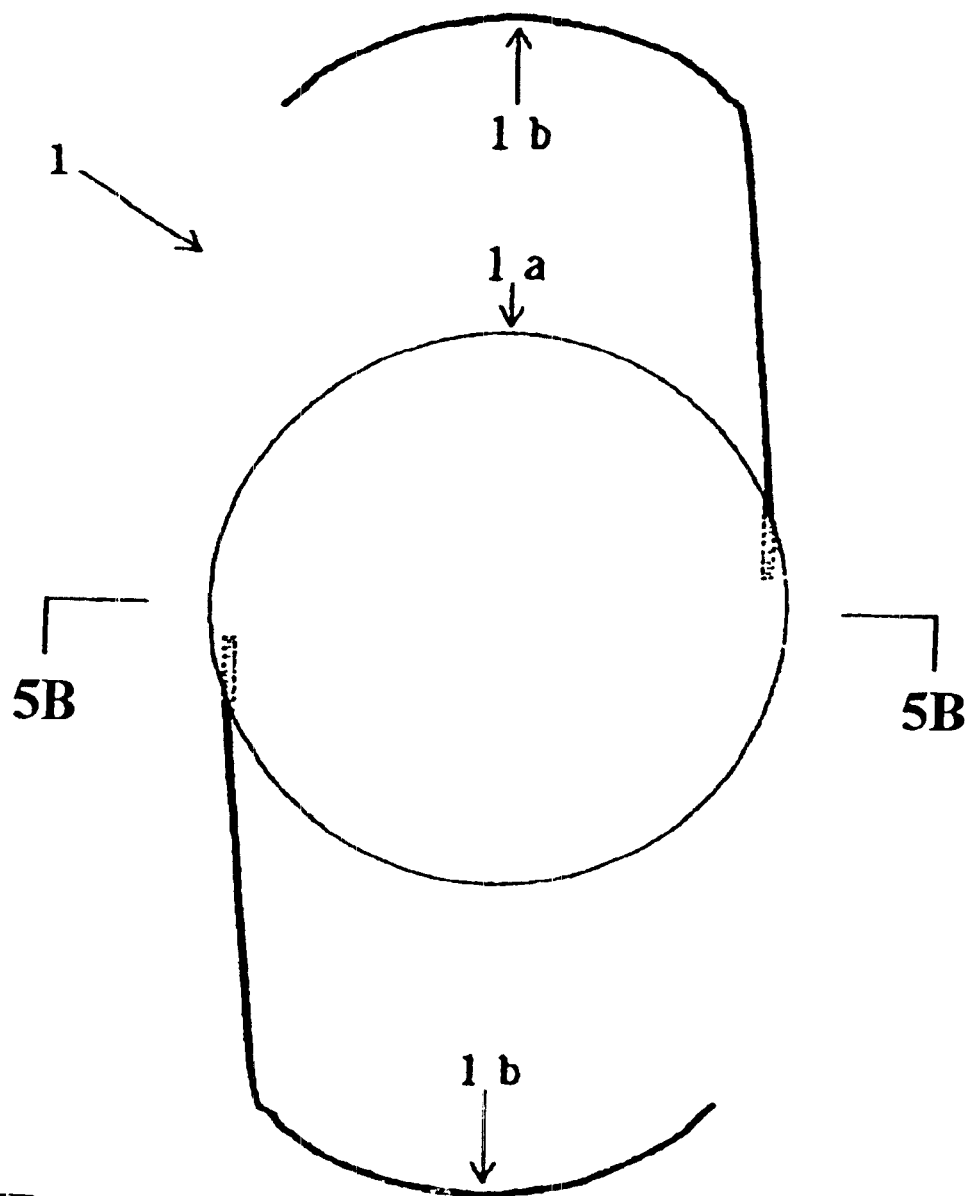
FIG. 5A is a top view of the intraocular lens used in an embodiment of the intraocular lens inspection method of the present invention.
Figure 5B:
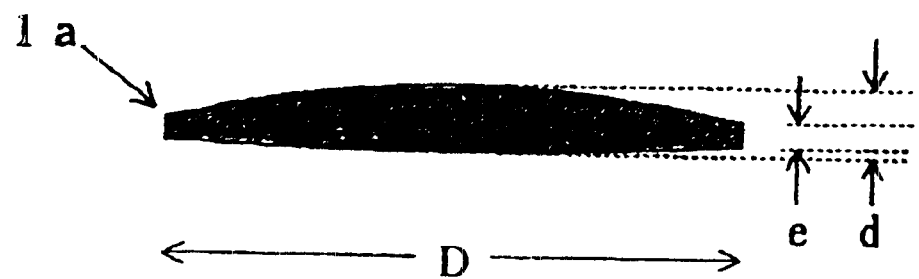
FIG. 5B is a sectional side view along line 5B—5B in FIG. 5A.
Figure 6:
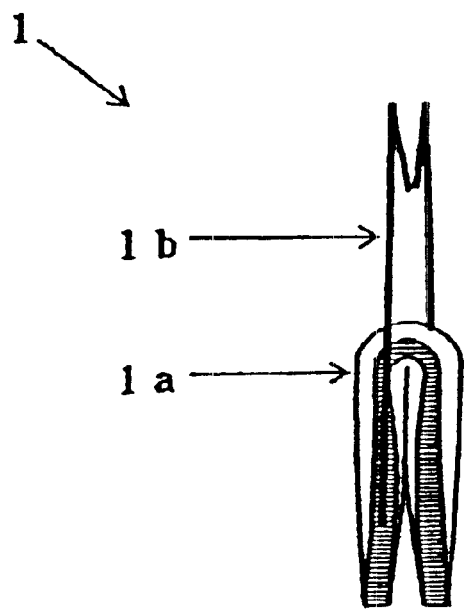
FIG. 6 is a side view showing the intraocular lens used in an embodiment of the intraocular lens inspection method of the present invention folded in the middle.
Figure 7:
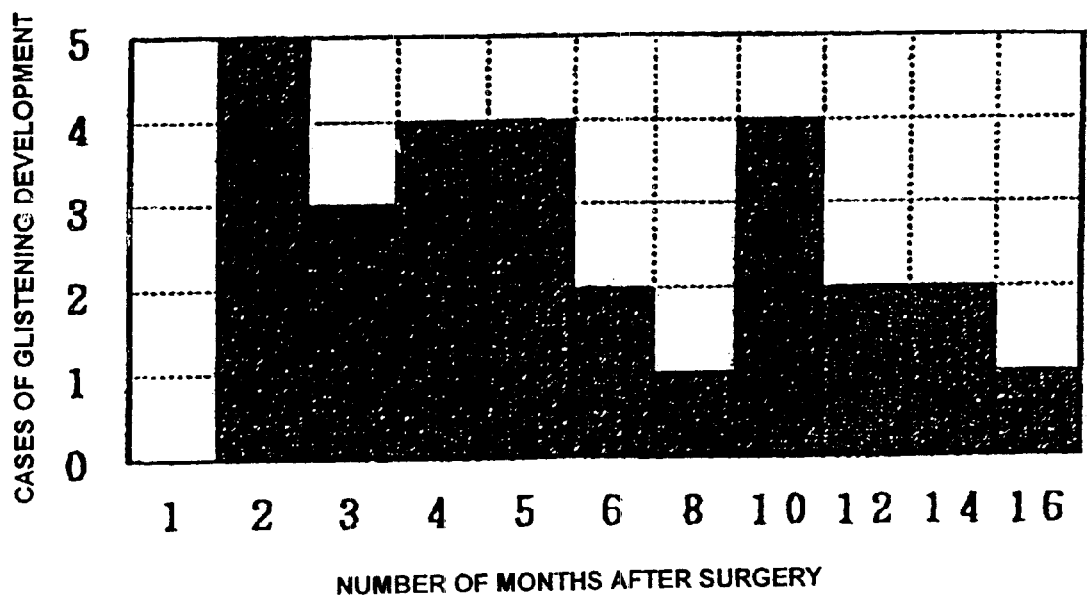
FIG. 7 is a histogram of the clinical glistening development period in the case of clinical use for comparison of the same type of intraocular lens as used in the intraocular lens inspection methods of an embodiment of the present invention.

FIG. 1 is a flowchart showing the processes of an embodiment of the intraocular lens inspection method of the present invention. FIG. 2A is a side view of part of the inspection mechanism for observing glistenings using a slit-lamp microscope of the intraocular lens inspection method. FIG. 2B is a diagram of an example of the field of vision in which the surface of the intraocular lens for inspection is inspected and observed with a microscope. FIG. 3 shows changes over time in the diameter of glistenings showing a method of determining the day on which glistenings develop. FIG. 4 is a histogram of the day on which clinically analogous glistenings develop as determined using the intraocular lens inspection method. FIG. 5A is a top view of an intraocular lens used in the intraocular lens inspection method, and FIG. 5B is a sectional side view taken along the line 5B—5B. FIG. 6 is a side view showing the intraocular lens folded in the center. FIG. 7 is a histogram of the clinical glistening development period in the case of clinical use for the purpose of comparison of the same type of intraocular lens as used in the intraocular lens inspection method.

Embodiments of the present invention will now be described with reference to the figures. As shown in the process flowchart in FIG. 1, the intraocular lens inspection method of the present invention is characterized in that:

after going through the process of intraocular lens extraction for inspection (S-1) whereby a lens is randomly extracted from a lot of intraocular lenses 1 that have been produced;

in the high-temperature liquid immersion process (S-10), the intraocular lens is immersed in physiological saline, which provides the same environmental body fluid as in the state of clinical use and is a sterile aqueous sodium chloride solution isotonic with this body fluid and is kept for approximately two hours at high temperature $T_h$ of approximately 50° C. such that the intraocular lens does not deteriorate using a first thermostatic cell such as an incubator, which is a thermostatic cultivation device;

then, promptly moving to a low-temperature liquid immersion process (S-20), the intraocular lens is removed and transferred to physiological saline at low-temperature $T_l$ of approximately 35° C., which provides approximately the same temperature as that clinically used, using a second thermostatic liquid cell, and this intraocular lens is observed macroscopically; and if changes are hardly detected, the lens is transferred to an inspection process (S-30) in which the intraocular lens is moved to the inside of a room kept at low temperature $T_l$ of approximately 35° C., the surface of the lens is gently washed with distilled water at the same temperature $T_l$ and magnified and observed under a microscope, such as slit-lamp microscope, and after observation, is directly returned to its original state (or into the physiological saline at low-temperature $T_l$), and when changes in the lens are observed over time with each observation and glistenings that are consistent in terms of the number and size are seen, it is judged that clinically analogous glistenings will develop.

The Intraocular lens 1, also commonly called an acrylic lens, used in the intraocular lens inspection method of the embodiment of the present invention is made from acrylic copolymer cross-linked resin lens body 1a and two polymethyl methacrylate (PMMA) resin J-shaped loops 1b that support this lens body at the posterior chamber. The dimensions of this lens body are a lens diameter of 6 mm, lens thickness of 0.75 mm, and edge thickness of 0.30 mm, and maximum diameter of these two loops is 13 mm. This corresponds to a lens power of biconvex +21D. The lens body is an acrylic copolymer cross-linked resin having a three-dimensional structure where a copolymer of phenylethyl acrylate and phenylethyl methacrylate is cross-linked with butanediol diacrylate. It has a refractive index of 1.55 and shows ultraviolet ray-absorbing capability. It is flexible with a Shore hardness (Shore A), which represents surface hardness, of 45, and as shown in FIG. 6, it can be folded in two. With respect to thermal properties, its glass transition temperature $T_g$ is 15.5 to 21.5° C., with there being a marked increase in volume expansion at this glass transition temperature $T_g$ or higher when compared to volume expansion at temperatures lower than $T_g$.

In the high-temperature liquid immersion process (S-10) of the intraocular lens inspection method of the embodiment of the present invention, the intraocular lens 1 is immersed in physiological saline (0.9 grams sodium chloride contained 100 ml pure water) and kept for approximately two hours at high temperature $T_h$ of approximately 50° C. No changes were seen in this lens when it was observed macroscopically.

In the low-temperature liquid immersion process (S-20) of the intraocular lens inspection method of the embodiment of the present invention, the intraocular lens 1 is transferred to physiological saline kept at low temperature $T_l$ of approximately 35° C. When the intraocular lens was observed macroscopically, the lens immediately became cloudy and then gradually cleared from the edges of the lens after several tens of minutes. Moreover, several round transparent areas were seen in this lens and large glistenings were detected in the center of these round transparent areas. Clouding of this lens disappeared and only large glistenings remained after several hours. These glistenings could not be detected macroscopically over time as well.

In the inspection process (S-30) of the intraocular lens inspection method of the embodiment of the present invention, the intraocular lens 1 is removed to inside a chamber kept at low temperature $T_l$ of approximately 35° C., and the surface is gently washed with distilled water at the same temperature $T_l$ in order to prevent precipitation of salt crystals from the physiological saline onto this lens surface. As shown in FIG. 2A, the lens is held in a holder 2c of a slit-lamp microscope 2, and illuminating light from illumination lamp 2b is irradiated onto the lens surface oblique from illumination optical axis 2f using a mirror 2e. As shown in FIG. 2B, the surface is magnified and observed for changes over time by determining the size of glistening 1c in viewing field 2g using microscope 2a. As shown in FIG. 3, the number of days from the time when the lens is transferred to the low-temperature liquid immersion process (S-20) until the diameter of the glistenings becomes constant is determined as the days of glistening development. The histogram of the clinically analogous day of glistening development of eight intraocular lens specimens randomly extracted for the inspection shown in FIG. 4 is confirmed. Glistening is seen with each of these intraocular lenses, and this glistening diameter is also approximately 10 $\mu$m. The average days of glistening development is approximately three days. Moreover, density at which the glistenings developed in the intraocular lenses was approximately 100/mm$^3$, corresponding to a clinical classification of grade 2. These glistenings were very analogous with the glistenings seen in clinical cases.

The clinical glistening development period histogram with clinical use was confirmed as shown in FIG. 7 in order to compare the same type of acrylic copolymer cross-linked resin intraocular lens used in the intraocular lens inspection method of the embodiment of the present invention. The post-surgical observation time was a maximum of 20 months and a minimum of five months (average of 13.1 months). The development of glistening during this time (density of approximately 50 glistenings or more, clinical classification of grade 1 or higher) was confirmed in 28 of 49 eyes (57%). When the time at which development of glistenings was first confirmed serves as the glistening development time, there were no cases in which the glistening developed one month after surgery, but glistenings did develop at some time after two months after surgery, with the greatest delay in glistening development being 16 months after surgery. The average glistening development period in these 28 eyes was 6.6 months.

The development of even some glistening was not observed when the intraocular lens inspection method of the present invention was used for intraocular lens 1, lens body 1a of which was made from polymethyl methacrylate; and there are no reported cases of the development of glistenings even when this intraocular lens is used clinically. Therefore, this lens is not in contradiction to this intraocular lens inspection method. However, the frequency with which these intraocular lenses are used has decreased recently, and the reason for this is that these intraocular lenses are rigid and cannot be folded in two; and therefore, they have a disadvantage in that the surgical incision is wide. Moreover, they have a double disadvantage in that the refractive index of PMMA resin is 1.49, which is smaller than the refractive index of 1.55 of the above-described acrylic copolymer cross-linked resin and, therefore, a thick lens of thickness d is required in order to obtain a lens of the same power.

The present invention is practiced in the manners described above and provides the following results:

With the intraocular lens inspection method of the present invention, it is possible to know the existence, extent, status, etc., of the development of glistenings attributed to internal structure, such as voids, etc., of intraocular lenses, depending on the material and production method used, using intraocular lenses that have been selected randomly from an intraocular lens production lot prior to clinical use. Therefore, it is possible to judge whether or not the lens should be accepted for or rejected from use prior to clinical use and to use safely, without any risk, the intraocular lens production lot clinically.

With the intraocular lens inspection method of the present invention, it is possible to guarantee a result that does not contradict to the clinical use, not only in terms of the existence of glistenings, but also in terms of their number and size. It is also possible to detect glistenings analogous to those that will develop in clinical cases in a short amount of time and inspect lenses with a markedly curtailed development time in comparison to when used clinically.

With the method of inspecting intraocular lenses of the present invention, it is possible to know the existence, extent, status, etc., of development of glistenings attributed to the internal structure, such as voids, etc., of intraocular lenses, depending on materials and production methods. Therefore, the method can be used for the development of new materials for the lens body.

What is claimed is:

1. An intraocular lens inspection method comprising the steps of:

executing an inspection intraocular lens extracting process for selecting a plurality of intraocular lens by way of a random extraction from an intraocular lens production lot;

performing a high-temperature liquid immersion process for immersing said intraocular lens, which has been selected, in physiological saline isotonic having same environmental body fluid as in a clinical use, and keeping said intraocular lens for a specific amount of time at high temperature $T_h$ such that deterioration of the lens does not occur;

promptly moving to a low-temperature liquid immersion process for removing said intraocular lens and transferring said removed intraocular lens to physiological saline that has been kept at low temperature $T_l$, which is approximately the same temperature as in a clinical use, and then observing said intraocular lens macroscopically; and upon observation of no changes in said intraocular lens, moving to an inspection process for removing said intraocular lens from said physiological saline and putting said intraocular lens in a room kept at said low-temperature $T_l$, gently washing a surface of said intraocular lens and then magnifyingly observing said intraocular lens by a microscope; and after observation, returning said intraocular lens quickly to an original state thereof, observing changes in said intraocular lens over time, and, upon a detection of glistenings that are consistent in terms of number and size, making a judgment that clinically analogous glistenings will develop.

* * * * *